(12) United States Patent
Shin et al.

(10) Patent No.: US 11,571,114 B2
(45) Date of Patent: Feb. 7, 2023

(54) DETACHABLE ENDOSCOPE

(71) Applicant: TAEWOONG MEDICAL CO., LTD., Gimpo-si (KR)

(72) Inventors: Kyong Min Shin, Gyeonggi-do (KR); Sung Hwan Park, Gimpo-si (KR); Hyun Soo Ji, Gimpo-si (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 231 days.

(21) Appl. No.: 17/014,364

(22) Filed: Sep. 8, 2020

(65) Prior Publication Data

US 2021/0068626 A1 Mar. 11, 2021

(30) Foreign Application Priority Data

Sep. 11, 2019 (KR) .................. 10-2019-0112948

(51) Int. Cl.
*A61B 1/00* (2006.01)
*A61B 1/005* (2006.01)
*A61B 1/05* (2006.01)
*A61B 1/06* (2006.01)
*A61B 1/12* (2006.01)

(52) U.S. Cl.
CPC ........ *A61B 1/00105* (2013.01); *A61B 1/0052* (2013.01); *A61B 1/00112* (2013.01); *A61B 1/05* (2013.01); *A61B 1/06* (2013.01); *A61B 1/12* (2013.01)

(58) Field of Classification Search
CPC ............ A61B 1/00105; A61B 1/00112; A61B 1/00121; A61B 1/00128; A61B 1/0051; A61B 1/0052; A61B 1/0057
See application file for complete search history.

(56) References Cited

U.S. PATENT DOCUMENTS

| 4,919,112 A | * | 4/1990 | Siegmund | ............ | A61B 1/0052 600/146 |
| 2008/0262309 A1 | * | 10/2008 | Miyoshi | ............... | A61B 1/0052 600/146 |
| 2013/0096384 A1 | * | 4/2013 | Arai | .................... | G02B 23/2476 600/144 |

FOREIGN PATENT DOCUMENTS

| KR | 10-0673412 B1 | 1/2007 |
| KR | 10-1091999 B1 | 12/2011 |
| KR | 10-1783225 B1 | 9/2017 |

* cited by examiner

*Primary Examiner* — Aaron B Fairchild
(74) *Attorney, Agent, or Firm* — Bridgeway IP Law Group, PLLC; Jihun Kim

(57) ABSTRACT

A detachable endoscope includes an insertion unit including an illuminating and image pickup unit, an operation unit configured to bendingly operate a front end of the insertion unit, and a detachable unit configured to detachably couple the insertion unit and the operation unit to each other, wherein the detachable unit comprises: a first detachable module disposed at the insertion unit in such a manner as to be connected to respective one ends of first and second operating wire and third and fourth operating wires juxtaposedly arranged in the insertion unit; and a second detachable module disposed at the operation unit in such a manner as to be connected to respective both ends of upper and lower chains wound around upper and lower sprockets of the operation unit.

6 Claims, 9 Drawing Sheets

DETACHABLE ENDOSCOPE

BACKGROUND OF THE INVENTION

1. Field of the Invention

The present invention relates to an endoscope. More specifically, the present invention relates to a detachable endoscope which can simply couple an insertion unit inserted into a body cavity to an operation unit that bendingly operates a front end of the insertion unit with each other for use in endoscopic surgery, and simply decouple the operation unit and the insertion unit from each other for storage or disinfect them for re-use after endoscopic surgery.

2. Description of Related Art

In general, surgery employing an endoscope, i.e., endoscopic surgery is performed such that a surgeon inserts a camera-equipped endoscope and a surgical instrument into a small body cavity without a making large incision, and then examines a patient's affected area through an image picked up by the endoscope inside the body.

In particular, endoscopic surgery originated from laparoscopic surgery has an advantage in that since a scarred part is relatively small owing to a small incised part and the amount of bleeding is less as compared to laparotomy, the recovery time of the patient is fast after endoscopic surgery.

In recent years, medical technologies have been developed enough to enable endoscopic surgery in almost all surgeries needing laparotomy as well as the case increases in which endoscopic surgery is applied in other medical fields.

A conventional general endoscope is configured in such a manner that an insertion unit inserted into the body cavity and an operation unit for controlling the insertion unit are integrally formed with each other, and a plurality of conduits and guides are installed in the insertion unit and the operation unit in such a manner as to internally pass through each unit, particularly an image pickup device such as an expensive CCD is provided at a front end of the insertion unit. However, such a conventional endoscope entails a problem in that it is difficult to separate only the insertion unit from the operation unit to replace it with a new one.

Patent Document 1: KR10-0673412 B1
Patent Document 2: KR10-1091999 B1
Patent Document 3: KR10-1783225 B1

Patent documents 1 to 3 disclose various types of detachable endoscopes that can couple an insertion unit inserted into a body cavity and an operation unit that operates the insertion unit to each other in use, or decouple the insertion unit and the operation unit from each other for storage so as to keep up with a recent trend toward more enhanced hygienic function of the endoscopes used for medical purposes.

However, the detachable endoscopes disclosed in the above Patent Documents is required to include a pressing member such as a button in a connection unit and release a hooking connection between the insertion unit and the operation unit, established by the connection unit using the pressing member in order to decouple the insertion unit and the operation unit from each other after endoscopic surgery in a structure in which the operation unit and the insertion unit are detachably coupled to each other by means of the connection unit, resulting in an increase in complexity of the structure of the connection unit that detachably interconnects the operation unit and the insertion unit and thus an increase in manufacturing costs of the endoscope.

In addition, the conventional detachable endoscopes involves a problem in that a hook release button additionally provided at the connection unit and an accessory structure associated therewith may lead to an increase in the number of the entire components of the connection unit, to a mechanical erroneous operation of the hook release button during the use of the surgical endoscope, and to an increase in expenses required to maintain and repair the connection unit.

SUMMARY OF THE INVENTION

The present invention has been made to solve the above-mentioned problems associated with the prior art, and it is an object of the present invention to provide a detachable endoscope in which a separate hooking connection between coupling members and coupled members which correspond to each other is selectively established by an external force applied to an operation unit upon selective rotational operation of the operation unit for bendingly operating a front end of an insertion unit in vertical and horizontal directions without having to additionally provide a separate hooking connection means.

Another object of the present invention is to provide a detachable endoscope in which a separate hooking connection release between coupling members and coupled members is selectively achieved upon release of an external force applied to an operation unit for bendingly operating a front end of an insertion unit in vertical and horizontal directions without having to additionally provide a separate hooking connection release means.

The technical problems to be solved in the present invention are not limited to the above-mentioned technical problems, and the other technical problems that are not mentioned in the present invention will be apparently understood by one of ordinary skill in the art in the technical field to which the present invention pertains from the following description.

To achieve the above objects, in a preferred embodiment, the present invention provides a detachable endoscope which includes an insertion unit including an illuminating and image pickup unit, an operation unit configured to bendingly operate a front end of the insertion unit, and a detachable unit disposed between the insertion unit and the operation unit and configured to detachably couple the insertion unit and the operation unit to each other, wherein the detachable unit comprises: a first detachable module disposed at the insertion unit in such a manner as to connected to respective one ends of first and second operating wire and third and fourth operating wires juxtaposedly arranged in the insertion unit; and a second detachable module disposed at the operation unit in such a manner as to be connected to respective both ends of upper and lower chains wound around upper and lower sprockets of the operation unit, wherein the second detachable module comprises: a second module main body disposed within a front end of the operation unit and having first, second, third and fourth rectilinear through-bores penetratingly formed longitudinally therein; first, second, third and fourth connecting shafts respectively disposed reciprocatingly within the first, second, third and fourth rectilinear through-bores in such a manner as to be connected at respective one ends thereof to the both ends of the upper and lower chains by means of first, second, third and fourth connecting wires; and first, second, third and fourth coupled members respectively disposed at the other ends of the first, second, third and fourth connecting shafts in such a manner as to be selectively hookingly connected to first, second, third and fourth coupling members disposed at the first detachable module, wherein the first, second, third and fourth coupling members are configured to be inserted into inner hollow parts formed in the first, second, third and fourth coupled members such that, when at least one of the first, second, third and fourth connecting shafts is rotationally displacedrotated unidirectionally, the respective coupled member and its corresponding coupling member are connected to each other by a hooking connection, and the remaining coupled members and the remaining coupling members are maintained in a hooking connection standby state where the hooking connection is released.

In the detachable endoscope of the present invention, the first, second, third and fourth connecting shafts may respectively include: one or more operating bars reciprocatingly inserted into the first, second, third and fourth rectilinear through-bores and respectively including one or more elastic members; one or more guide pins disposed at one ends of the operating bars so as to rotationally displace the operating bars while moving guidingly in a curved pattern along compound guide slits formed to be incised on the second module main body; and first, second, third and fourth coupled members respectively disposed at one ends of the operating bars having the guide pins formed thereon so as to selectively hookingly connected to the first, second, third and fourth coupling members.

In the detachable endoscope of the present invention, the second module main body may include: a main body block having the first, second, third and fourth rectilinear through-bores penetratingly formed longitudinally therein and the compound guide slits formed to be incised on an outer surface thereof; a first covering plate disposed at one end of the main body block and having a plurality of first through-holes penetratingly formed therein to allow respective one ends of the first, second, third and fourth connecting shafts to advance to and retract from the first through-holes; and a second covering plate disposed at the other end of the main body block corresponding to the first detachable module, and having a plurality of second through-holes penetratingly formed therein to correspond to distal ends of the first, second, third and fourth rectilinear through-bores.

In the detachable endoscope of the present invention, the elastic members may supportingly abut at one ends thereof against an inner surface of the first covering plate, and supportingly abut at the other ends thereof against larger diameter parts of the operating bars, which have the guide pins formed thereon.

In the detachable endoscope of the present invention, the compound guide slits may include: curved sections formed of curved slits extending in a curved pattern from both sides of the main body block to the top and bottom surfaces thereof, and linear sections formed of rectilinear slits longitudinally extending by a predetermined length on the top and bottom surfaces of the main body block.

In the detachable endoscope of the present invention, the first, second, third and fourth coupled members may include slot-shaped hooking holes formed therein to expose the inner hollow parts toward the first, second, third and fourth coupling members, and the first, second, third and fourth coupling members may include plate-shaped hooking pieces formed at distal ends thereof so as to be widened at front ends thereof to both sides.

EFFECTS OF THE INVENTION

The detachable endoscope according to a preferred embodiment of the present invention as constructed above has the following effects.

Any one of a plurality of connecting shafts is selectively rotationally displaced by an external force applied to an operation unit upon selective rotational operation of the operation unit so that the coupling members and the coupled members can be hookingly connected to each other without having to additionally provide a separate hooking connection means, and thus a connecting operation of selectively hookingly interconnecting the coupling members of the first detachable module and the coupled members of the second detachable module and a bending operation of bendingly operating a front of the insertion unit unidirectionally or bidirectionally can be performed as a series of sequential operations, thereby improving convenience in use.

Any one of a plurality of connecting shafts, selectively rotationally displaced, returns to its original position by an elastic restoring force of a corresponding elastic member upon release of an external force applied to the operation unit so that the hooking connection between the coupling members and the coupled members can be released without having to additionally provide a separate hooking connection release means, and thus the coupling members of the first detachable module and the coupled members of the second detachable module and can return to a hooking-connection release state and simultaneously the operating state of the coupling members and the coupled members can be converted into a hooking connection standby state for performing the bending operation of bendingly operating a front of the insertion unit unidirectionally or bidirectionally by the transmission of external force from the operation unit, thereby improving convenience in use.

The elimination of the necessity of configuring an additional structure such as the hooking connection means or the hooking connection release mean like a button member can reduce the number of the entire components, resulting in a reduction in the manufacturing costs and thus a decrease in the maintenance and repair expenses.

When the insertion unit inserted into the body cavity is contaminated or malfunctions, it can be separated from the operation unit so as to be easily replaced with new one, thereby improving safety, and the contaminated insertion unit can be scrapped and disposed of and a new clean insertion unit is replaceably mounted on the detachable endoscope so that endoscopic surgery can be safely carried out.

BRIEF DESCRIPTION OF THE DRAWINGS

The above and other objects, features and advantages of the present invention will be apparent from the following detailed description of the preferred embodiments of the invention in conjunction with the accompanying drawings, in which.

DESCRIPTION OF THE PREFERRED EMBODIMENTS

Figure 1:
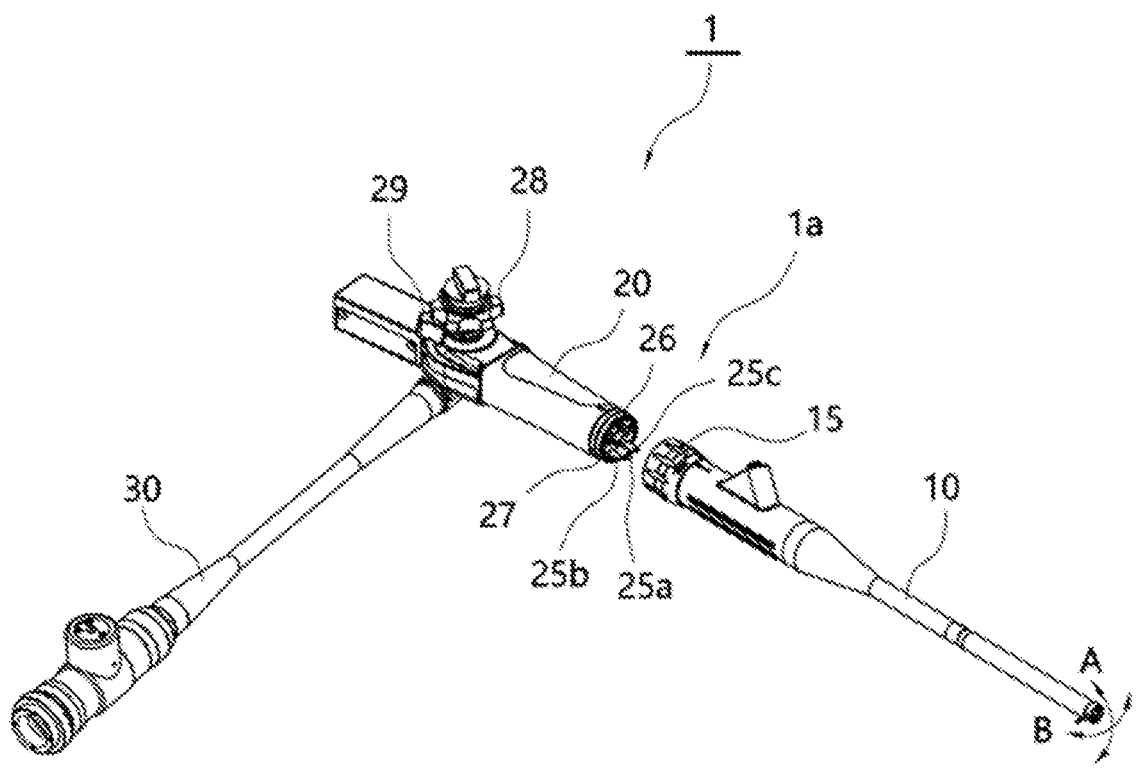
FIG. 1 is a schematic perspective view illustrating a detachable endoscope according to an embodiment of the present invention.

Hereinafter, embodiments of the present invention that can be easily implemented by those skilled in the art to which the present invention pertains will be described in detail with reference to the attached drawings. Further, if, in the description of the principles of the operation of preferred embodiments, detailed descriptions of well-known functions or configurations may unnecessarily make the gist of the present invention obscure, the detailed descriptions thereof will be omitted.

The same reference numerals are used throughout the different drawings to designate components performing the same or similar functions and operations.

Throughout the entire specification, a representation indicating that a first part is "connected" to a second part includes the case where the first part is "indirectly connected" to the second part with some other element interposed therebetween, as well as the case where the first part is "directly connected" to the second part. Further, a representation indicting that a certain part "includes" a certain element means that other elements may be further included in the certain part without excluding other elements unless a description to the contrary is specifically pointed out.

As shown in FIG. 1, a detachable endoscope 1 according to an embodiment of the present invention includes an insertion unit 10 that is inserted at a front end thereof into a body cavity when endoscopic surgery is performed, an operation unit 20 that includes a plurality of operation knobs, a universal joint 30 that is electrically connected to an endoscope control management system, and a detachable unit 1a that couples the insertion unit 10 and the operation unit 20 to each other before endoscopic surgery to mechanically interconnect them or mechanically decouples the insertion 10 and the operation unit 20 from each other after endoscopic surgery.

The insertion unit 10 is formed of a flexible tubular material so as to adjust a direction where it is inserted into a body cavity. The insertion unit 10 includes an illuminating and image pickup unit having a light source for illuminating the inside of the body cavity and an image sensor for capturing images of the body cavity at a front end thereof.

The operation unit 20 includes an upper operation knob 28 that bendingly operates the front end of the insertion unit inserted into the body cavity in a vertical direction, and a lower operation knob 29 that bendingly operates the front end of the insertion unit in a horizontal direction.

The operation unit 20 internally includes upper and lower sprockets provided at the upper and lower operation knobs, respectively, and upper and lower chains connected to the upper and lower sprockets so that a selective rotational motion of the upper and lower operation knobs is converted into a linear motion, and the upper and lower chains are connected to an inner side of a front end of the insertion unit by means of a plurality of operating wires disposed at the inside of the insertion unit.

Some of the plurality of operating wires disposed within the insertion unit is converted into a linear motion through the upper and lower sprockets rotated by the selective rotation of the upper and lower operation knobs by a user and the upper and lower chains performing a reciprocating rectilinear motion, so the front end of the insertion unit is bendingly operated in a vertical or horizontal direction in a body cavity in response to the linear motion of the operating wires.

The operation unit 20 includes an operation switch and an operation button for charging or discharging liquid or gas for washing and disinfection. In addition, the insertion unit 10 includes an inlet and outlet port formed at a rear end thereof to allow a surgical instrument such as an endoscopic treatment instrument having a clip to advance to or retract from the inside of the insertion unit therethrough, and a cap configured to open or close the inlet and outlet port, and the rear end of the insertion 10 is detachably coupled to a front of the operation unit 20 by means of the detachable unit.

Figure 2:
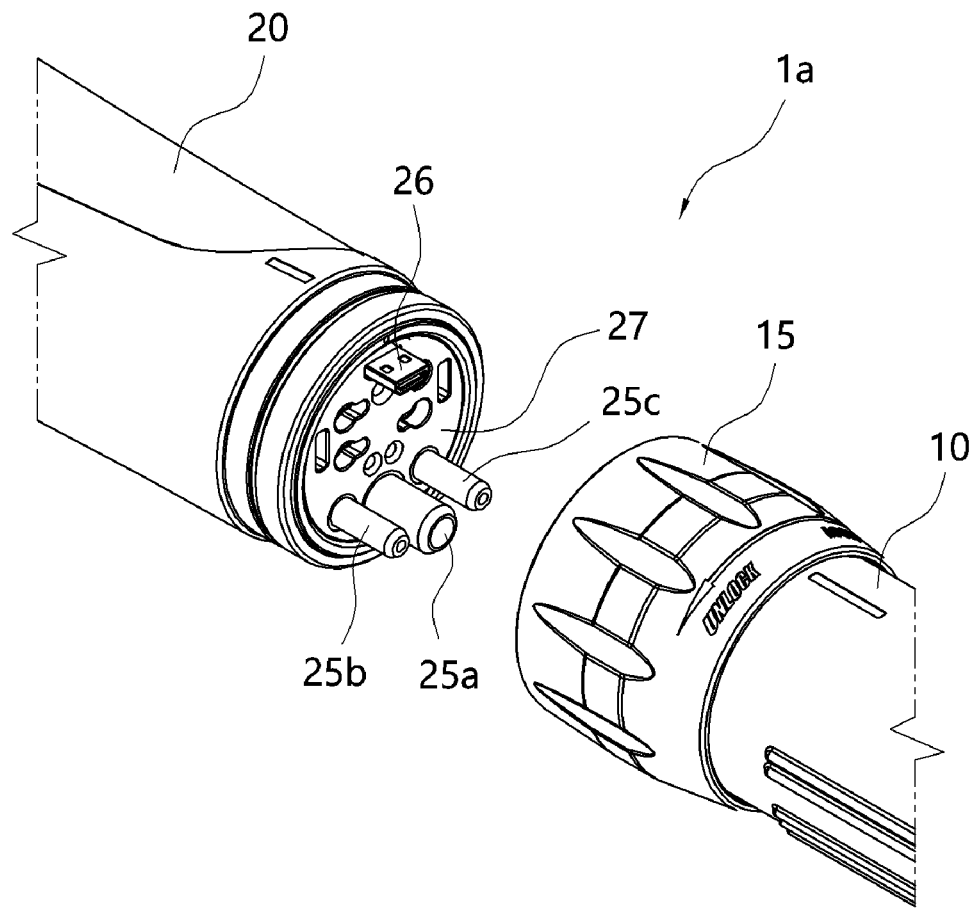
FIG. 2 is an exploded view illustrating a coupling part between a insertion unit and an operation unit of a detachable endoscope according to an embodiment of the present invention.

As shown in FIGS. 1 and 2, an end cover 27 provided at the front end of the operation unit includes an air supply channel 25b that supplies air, a water supply channel 25c that supplies water, and a suction channel 25a that sucks in water and air so as to be discharged to the outside. In addition, the end cover 27 includes a terminal 26 that is electrically connected to the illuminating and image pickup unit of the insertion unit 10. The insertion unit 10 is formed as a generally cylindrical housing and includes a ring-shaped coupling element 15 disposed at the rear end thereof so as to be screw-engaged with a female screw thread formed at the front end of the operation unit 20 formed as a cylindrical housing.

Figure 3:
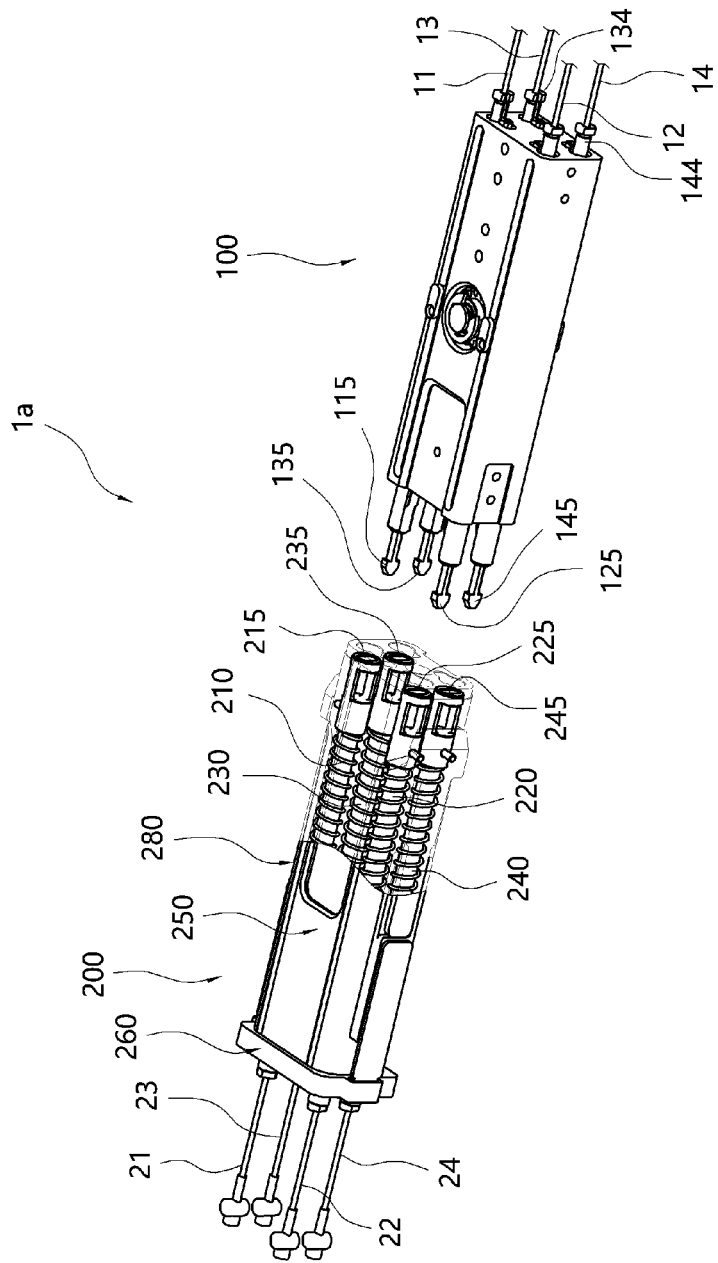
FIG. 3 is an exploded perspective view illustrating a detachable unit of a detachable endoscope according to an embodiment of the present invention.

As shown in FIGS. 2 and 3, the detachable endoscope 1 according to an embodiment of the present invention includes a detachable unit 1a that is configured to detachably couple the rear end of the insertion unit and the front end of the operation unit to each other.

The detachable unit 1a includes a first detachable module 100 insertedly disposed in the insertion unit 10 and a second detachable module 200 insertedly disposed in the operation unit 20 so as to be correspondingly coupled to the first detachable module 100.

The first detachable module 100 is connected to one ends of first and second operating wires 11 and 12 that are juxtaposedly arranged in the insertion unit to bendingly operate the front end of the insertion unit in a vertical direction (A) and is connected to one ends of third and fourth operating wires 13 and 14 that are juxtaposedly arranged in the insertion unit to bendingly operate the front end of the insertion unit in a horizontal direction (B).

The second detachable module 200 is connected to respective both ends of the upper and lower chains wound around the upper and lower sprockets that are rotated in forward and reverse directions in response to a rotational operation of the upper and lower operation knob 28 and 29 by means of first, second, third and fourth connecting wires 21, 22, 23 and 24.

Herein, although it has been illustrated and described that the first and second connection wires 21 and 22 connected to both ends of the upper chain wound around the upper sprocket bendingly operates the front end of the insertion unit in a vertical direction in cooperation with the first and second operating wires 11 and 12 justaposedly arranged in pair at an inner upper side of the insertion unit on the drawing sheet, and that the third and fourth connection wires 23 and 24 connected to both ends of the lower chain wound around the lower sprocket bendingly operates the front end of the insertion unit in a horizontal direction in cooperation with the third and fourth operating wires 13 and 14 justaposedly arranged in pair at an inner lower side of the insertion unit on the drawing sheet, the present invention is not limited thereto and the vertical and horizontal bending operations of the front end of insertion unit may be performed in a vice-versa manner depending on design specifications of an endoscope.

In addition, although it has been illustrated and described that the rotation of the upper and lower sprockets is performed by virtue of a manual rotational operation of a worker who grasps the upper and lower operation knobs provided at the operation unit, the present invention is not limited thereto and the rotation of the upper and lower sprockets may be performed in such a manner that a rotary shaft assembled with the upper and lower sprockets is connected to a drive means such as a motor and the drive means is controlled by a separate remote operation means such as a joystick.

Figure 4:
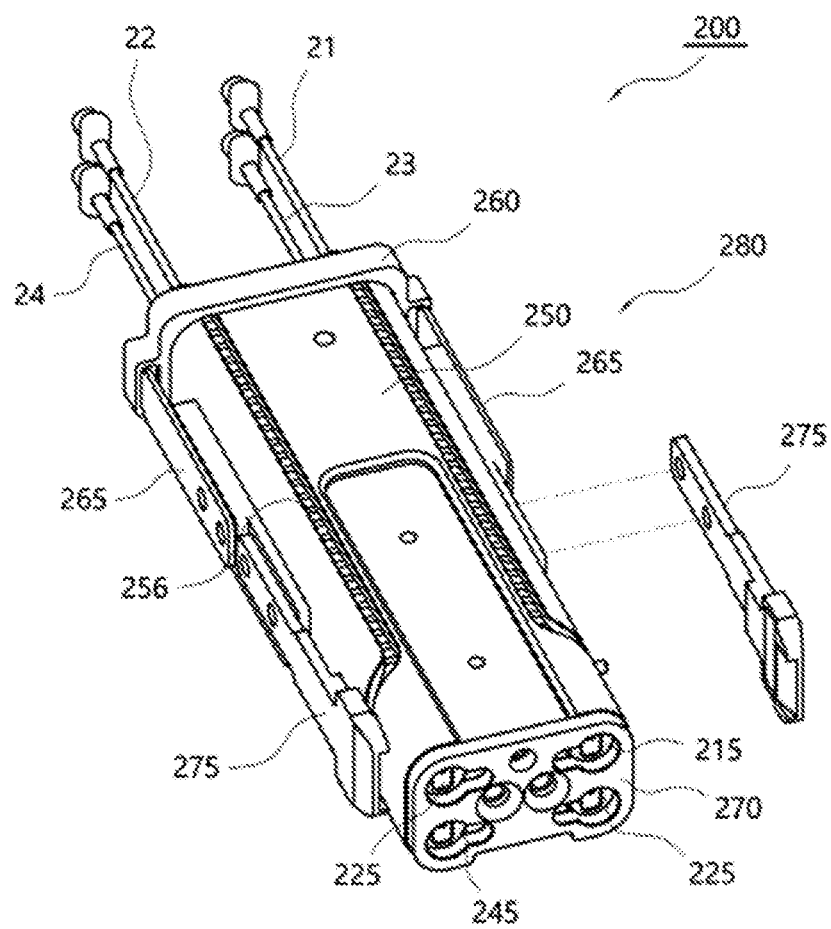
FIG. 4 is an assembled perspective view illustrating a second detachable module of a detachable unit of a detachable endoscope according to an embodiment of the present invention.
Figure 5:
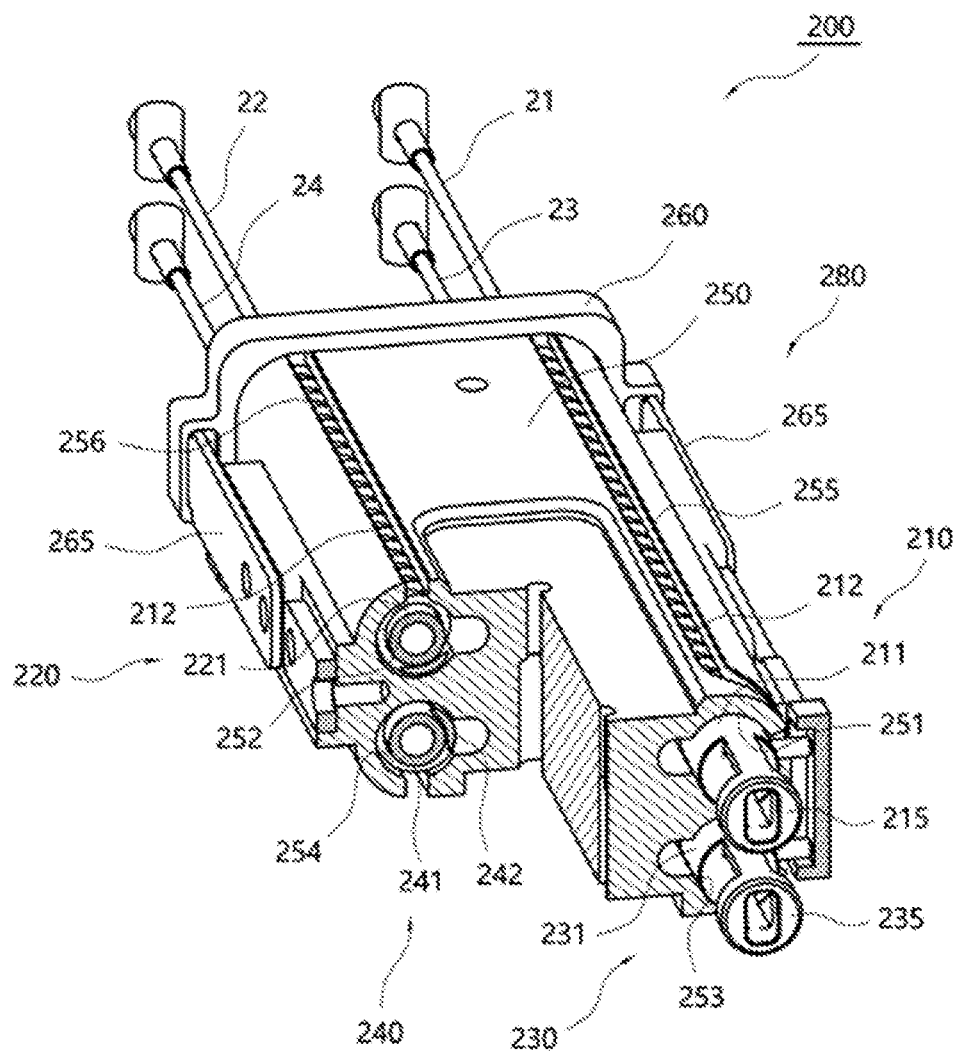
FIG. 5 is a cross-sectional perspective view illustrating a second detachable module of a detachable unit of a detachable endoscope according to an embodiment of the present invention.
Figure 6:
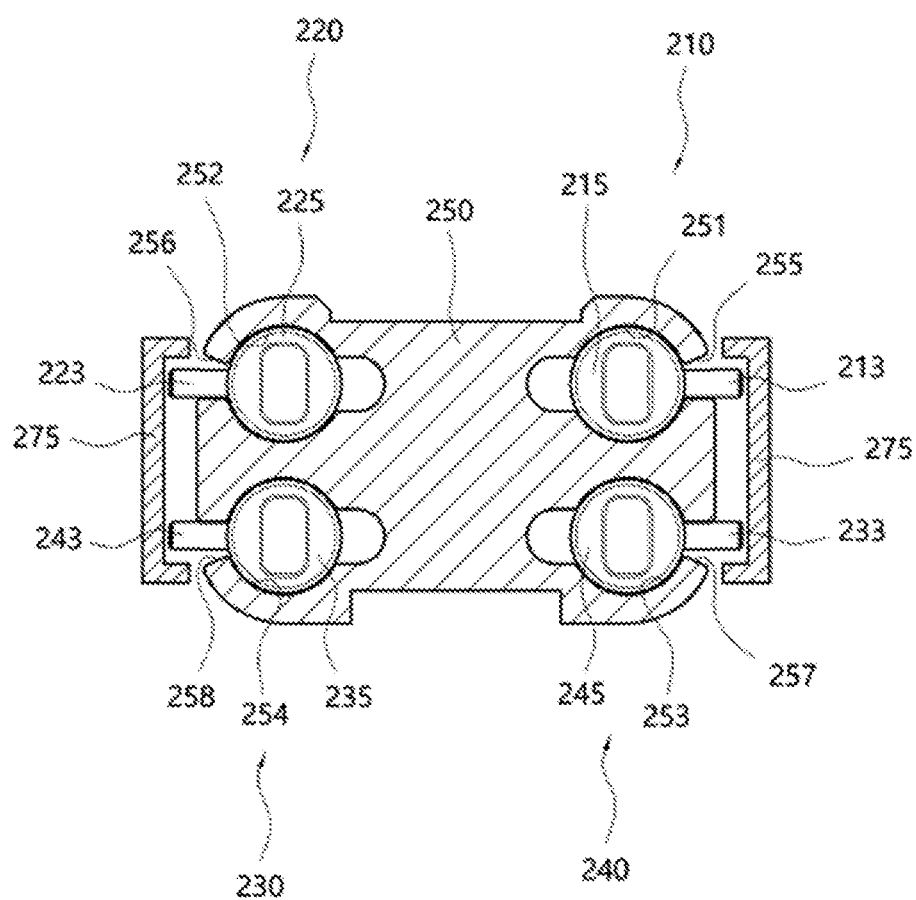
FIG. 6 is a vertical transverse cross-sectional view illustrating a second detachable module of a detachable unit of a detachable endoscope according to an embodiment of the present invention.
Figure 7:
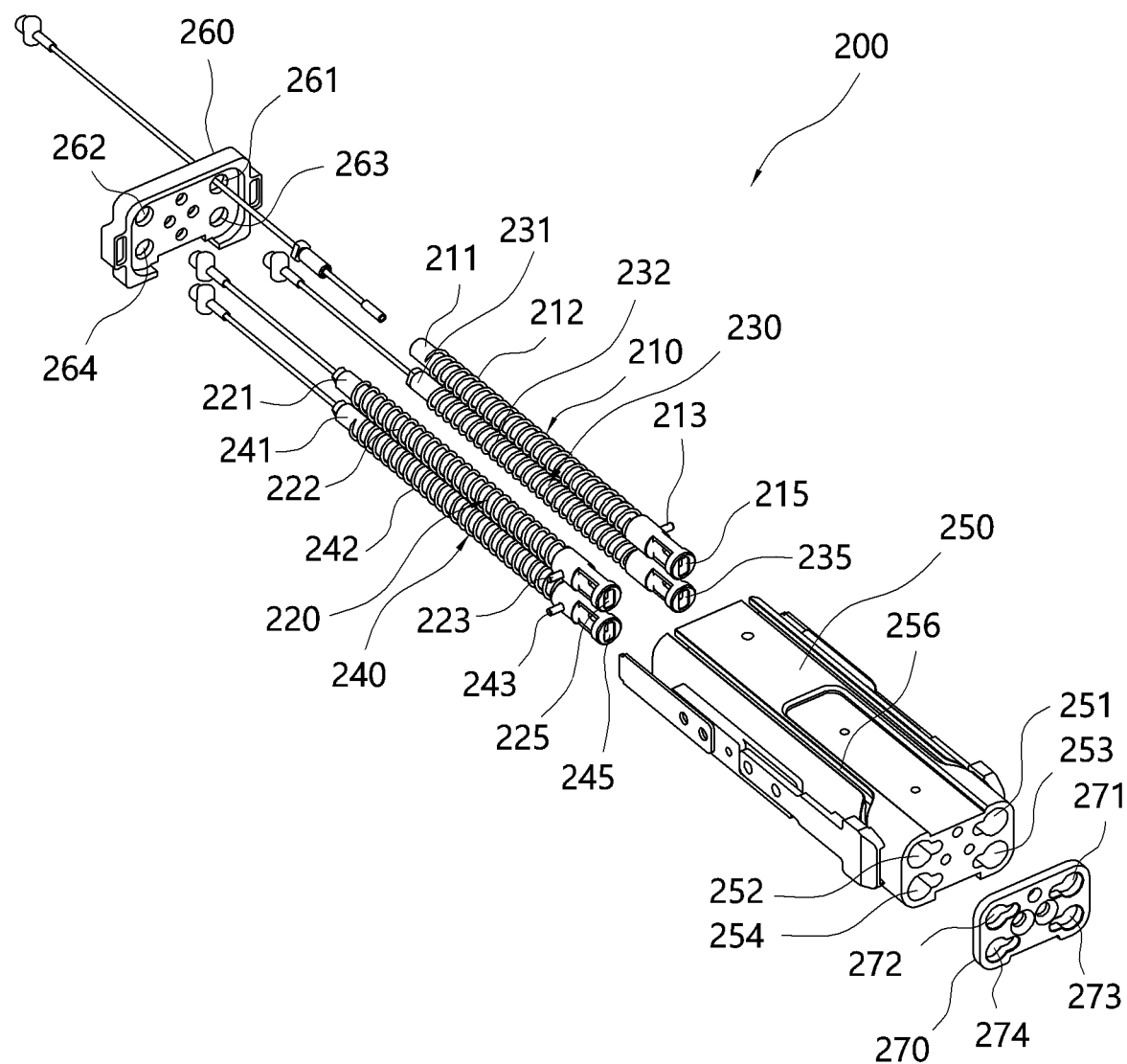
FIG. 7 is an exploded perspective view illustrating a second detachable module of a detachable unit of a detachable endoscope according to an embodiment of the present invention.

As shown in FIGS. 3, 4, 5. 6 and 7, the second detachable module 200 includes first and second connecting shafts 210 and 220 juxtaposedly arranged at an upper side thereof so as to operate in cooperation with the first and second operating wires, third and fourth connecting shafts 230 and 240 juxtaposedly arranged at a lower side thereof, and a second module main body 280 that internally accommodates the first and second connecting shafts 210 and 220 and the third and fourth connecting shafts 230 and 240.

The second module main body 280 includes a generally rectangular parallelepiped-shaped main body block 250 having first, second, third and fourth rectilinear through-bores 251, 252, 253 and 254 penetratingly formed longitudinally therein.

The second module main body 280 includes a first covering plate 260 disposed at one end of the main body block 250 and having a plurality of first through-holes 261, 262, 263 and 264 penetratingly formed therein to allow respective one ends of the first, second, third and fourth connecting shafts 210, 220, 230 and 240 corresponding to the first, second, third and fourth connecting wires 21, 22, 23 and 24 to advance to and retract from the first through-holes.

The second module main body 280 includes a second covering plate 270 disposed at the other end of the main body block 250 corresponding to the first detachable module 100, and having a plurality of second through-holes 271, 272, 273 and 274 penetratingly formed therein to correspond to distal ends of the first, second, third and fourth rectilinear through-bores 251, 252, 253 and 254.

Herein, the first covering plate 260 may include a first fixing bracket 265 disposed at both sides of one end of the main body block 250 so that the first covering plate 260 is assembled and fixedly mounted to the one end of the main body block 250, and a second fixing bracket 275 disposed at both sides of the other end of the main body block, corresponding to the second covering plate 270, so as to cover the guide pins that are positioned and are in a standby state in compound guide slits which will be described later to cover.

Herein, although it has been illustrated and described that the second fixing bracket 275 is fixedly mounted to both sides of the other end of the main body block, the second fixing bracket 275 may be fixedly mounted to other member provided in close proximity to the main body block.

The first, second, third and fourth coupled members 215, 225, 235 and 245 of the first, second, third and fourth connecting shafts 210, 220, 230 and 240 are exposed to the outside through the plurality of second through-holes penetratingly formed in the second covering plate.

The first and second connecting shafts 210 and 220 are rectilinear axial members that are connected at one ends thereof to the first and second connection wires 21 and 22 juxtaposedly arranged at the inner upper side of the operation unit, and are selectively hookingly connected at the other ends thereof to first and second coupling members 115 and 125 provided at first and second rack gears of the first detachable module 100. The third and fourth connecting shafts 230 and 240 are rectilinear axial members that are connected at one ends thereof to the third and fourth connection wires 23 and 24 juxtaposedly arranged at the inner lower side of the operation unit, and are selectively hookingly connected at the other ends thereof to third and fourth coupling members 135 and 145 provided at third and fourth rack gears of the first detachable module.

The first, second, third and fourth connecting shafts 210, 220, 230 and 240 include: a plurality of operating bars 211, 221, 231 and 241 having a generally circular cross section and including elastic members 212, 222, 232 and 242 such as coil springs, and reciprocatingly inserted into the first, second, third and fourth rectilinear through-bores 251, 252, 253 and 254 penetratingly formed longitudinally in the main body block 250 of the second module main body; a plurality of guide pins 213, 223, 233 and 243 disposed at one ends of the operating bars corresponding to the first detachable module so as to rotationally displace the operating bars while moving guidingly in a curved pattern along compound guide slits 255, 256, 257 and 258 formed to be incised on both side faces of the main body block 250 of the second module main body 280; and first, second, third and fourth coupled members 215, 225, 235 and 245 disposed at one ends of the operating bars having the guide pins formed thereon so as to selectively hookingly connected to the first, second, third and fourth coupling members 115, 125, 135 and 145 provided at the first, second, third and fourth rack gears.

In this case, the inner diameters of the first, second, third and fourth rectilinear through-bores 251, 252, 253 and 254 penetratingly formed in the main body block are preferably dimensioned to be relatively larger than the outer diameters of the operating bars having the elastic members such as coil springs fitted therearound.

Each of the guide pins 213, 223, 233 and 243 is preferably formed on a larger diameter part of each of the operating bars, which has the outer diameter relatively larger than the outer diameter of each of the operating bars so as to abut against the inner circumferential surface of each of the first, second, third and fourth rectilinear through-bores 251, 252, 253 and 254.

The elastic members 212, 222, 232 and 242 provided on the operating bar supportingly abuts at one ends thereof against an inner surface of the first covering plate 260 assembled to one end of the main body block, and supportingly abut at the other ends thereof against the larger diameter parts of the operating bars having the guide pins 213, 223, 233 and 243 formed thereon.

Thus, in the process in which the first, second, third and fourth connecting shafts reciprocatingly moves along the first, second, third and fourth rectilinear through-bores 251, 252, 253 and 254 penetratingly formed in the main body block, when the distance between the inner surface of the first covering plate and the larger diameter part of the operating bar becomes short, the elastic members 212, 222, 232 and 242 formed on the operating bars are compressingly deformed to generate elastic restoring forces that return the operating bars to their original positions.

Each of the first, second, third and fourth rectilinear through-bores 251, 252, 253 and 254 may include a generally circular guide bore and an extension bore formed extending outwardly from the guide bore to prevent occurrence of interference with the first, second, third and fourth rack gears, each of which includes a rectilinear rack bar and a plurality of gear teeth formed on a rack bar.

Similarly, each of the first and second through-holes penetratingly formed in the first and second covering plates assembled to both ends of the main body block 250 includes a circular guide hole and an extension hole formed extending outwardly from the guide hole.

The first, second, third and fourth coupled members 215, 225, 235 and 245 include slot-shaped hooking holes formed to expose inner hollow parts formed at one ends of the first, second, third and fourth connecting shafts adjacent to the guide pins toward the first, second, third and fourth coupling members of the first detachable module, and the first, second, third and fourth coupling members 115, 125, 135 and 145 include plate-shaped hooking pieces formed at distal ends thereof so as to extend by a predetermined length from ends of the first, second, third and fourth rack gears and to be widened at front ends thereof to both sides.

Further, the guide pins 213, 223, 233 and 243 disposed at one ends of the first, second, third and fourth connecting shafts in proximity to the first, second, third and fourth coupled members are assembled so as to guidingly move along the compound guide slits 255, 256, 257 and 258 formed to be incised on the outer surfaces of both sides of the main body of the second module main body 280. The compound guide slits 255, 256, 257 and 258 include curved sections formed of curved slits extending in a curved pattern from both sides of the main body block to the top and bottom surfaces thereof, and linear sections formed of rectilinear slits longitudinally extending by a predetermined length on the top and bottom surfaces of the main body block.

Accordingly, in the process in which the guide pins formed on the operating bars of the first, second, third and fourth connecting shafts move curvedly along the curved slits at the curved sections by an external force, the operating bars of the first, second, third and fourth connecting shafts move linearly while being rotationally displaced unidirectionally in the first, second, third and fourth rectilinear through-bores.

In this case, the slot-shaped hooking holes of the first, second, third and fourth coupled members disposed at the ends of the operating bars that are rotationally displaced are arranged in a crossing shape with a phase difference of 90 degrees to the hooking pieces of the first, second, third and fourth coupling members that advance to the inside of the inner hollow parts and are in a standby state.

Such hooking connections between the slot-shaped hooking holes of the first, second, third and fourth coupled members and the hooking pieces of the first, second, third and fourth coupling members are established at the time point when the compound guide slits are switched from the curved slits to the linear slits.

Subsequently, when the guide pins move linearly by a predetermined distance along the linear slits in the linear sections by an external force, the operating bars of the first, second, third and fourth connecting shafts move linearly in the first, second, third and fourth rectilinear through-bores in a state where a hooking connection between the slot-shaped hooking holes and the hooking pieces has been completed.

Figure 8A:
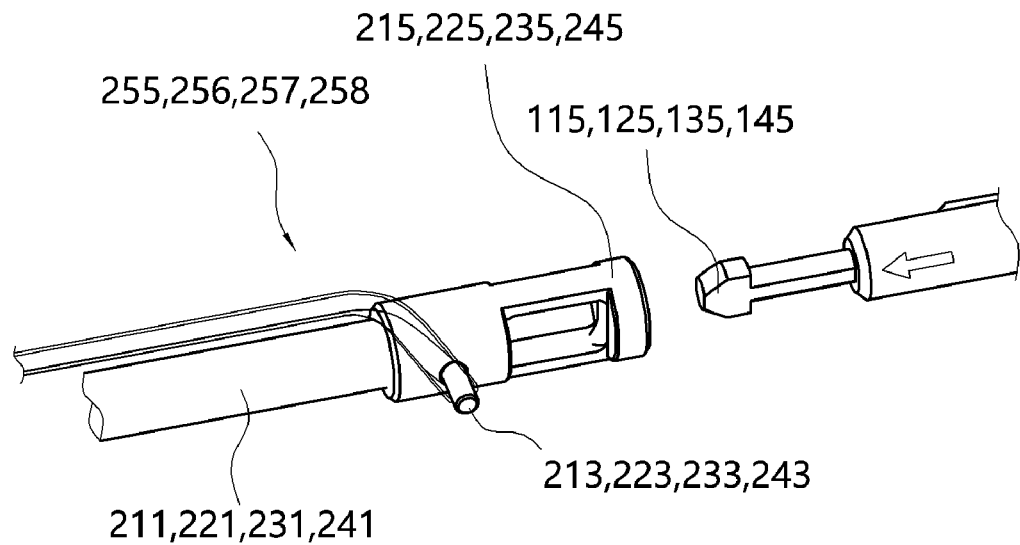
FIGS. 8a, 8b and 8c illustrate the operating state of a second detachable module of a detachable unit of a detachable endoscope according to an embodiment of the present invention.

By virtue of the hooking connection between the first, second, third and fourth coupled members of the second detachable module 200 and the first, second, third and fourth coupling members of the first detachable module 100 as constructed above, first, when the front end of the operation unit 20 and the rear end of the insertion unit 10 confront each other, the slot-shaped hooking holes of the first, second, third and fourth coupled members disposed at the front ends of the first, second, third and fourth connecting shafts confront the hooking pieces of the first, second, third and fourth coupling members disposed at the rear ends of the first, second, third and fourth rack gears in a one-to-one corresponding manner as shown in FIG. 8a.

In this case, the slot-shaped hooking holes of the first, second, third and fourth coupled members 215, 225, 235 and 245 and the hooking pieces of the first, second, third and fourth coupling members 115, 125, 135 and 145 confront each other in a vertical arrangement state.

Figure 8B:
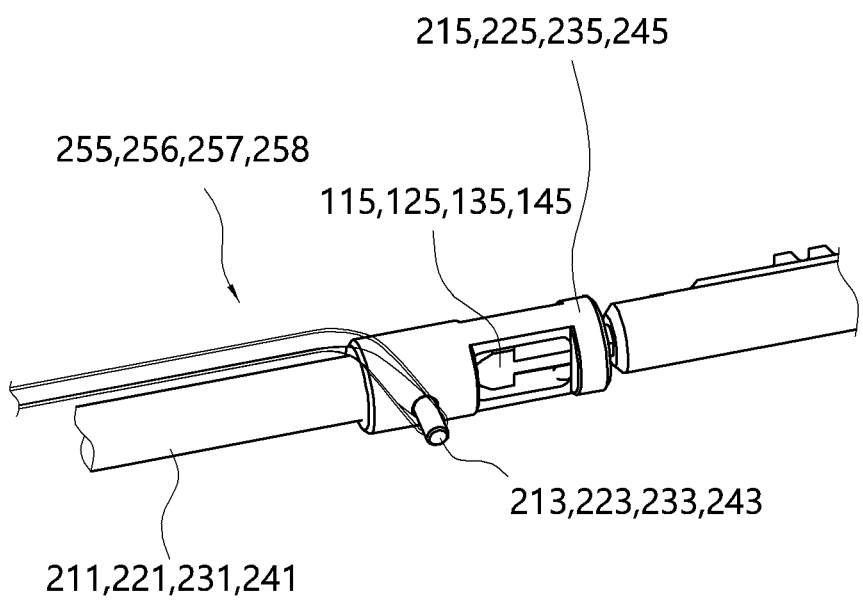

Thereafter, when the front end of the operation unit having the second detachable module and the rear end of the insertion unit having first detachable module are coupled to each other, the hooking pieces of the first, second, third and fourth coupling members 115, 125, 135 and 145 advance to the inner hollow parts formed in the first, second, third and fourth connecting shafts in an unhooked state through the slot-shaped hooking holes of the first, second, third and fourth coupled members 215, 225, 235 and 245 so that the hooking pieces are maintained in the same vertical arrangement state as that of the slot-shaped hooking holes as shown in FIG. 8b.

In other words, in the state where the outer housings are mechanically connected to the external surfaces by a ring-shaped coupling element interposed between the front end of the operation unit and the rear end of the insertion unit, the hooking pieces of the first, second, third and fourth coupling members disposed at one ends of the first, second, third and fourth rack gears are positioned without any interferences in the internal spaces defined by the inner hollow parts of the first, second, third and fourth coupled members disposed at one ends of the first, second, third and fourth connecting shafts, so that the hooking pieces are in a standby state for the purpose of hooking connection.

Figure 8C:
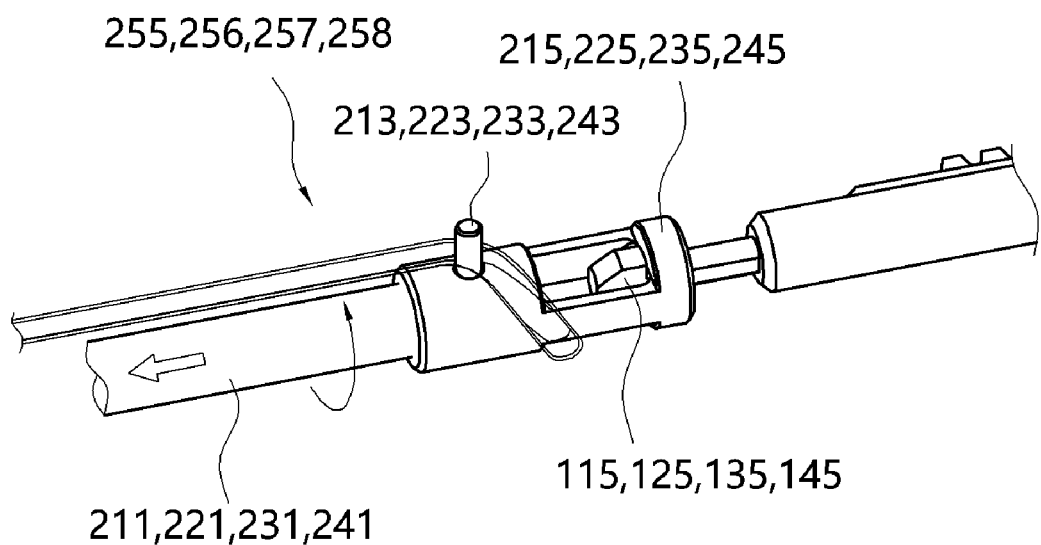

In this state, as shown in FIG. 8c, when a user selects any one of the upper and lower operation knobs and rotates the selected operation knob, any one of the first, second, third and fourth connecting shafts assembled to the first, second, third and fourth rectilinear through-bores formed in the main body block of the second module main body is pulled to the left on the drawing sheet by an external force generated upon the rotation of the selected operation knob, it is rotationally displaced while moving in a state of being pulled in proportional to the amount of rotation of the operation knob.

On the other hand, in a state where no rotation of the remaining operation knobs other than the selected operation knob occurs, the remaining connection shafts are maintained in a standby state to advance to the inside of the remaining rectilinear through-bores as shown in FIG. 8a, so that the hooking pieces of the coupling members is maintained in a hooking standby state for the purpose of establishing a hooking connection by being positioned in the inner hollow parts of the remaining coupled members.

Such a hooking standby state is the same as a hooking-connection release state where no hooking connection between the hooking pieces of the coupling members and the slot-shaped hooking holes of the coupled members is established.

In other words, when any one of the first, second, third and fourth connecting shafts is selected and pulled toward the operation unit by an external force caused by the selective rotation of any one of the upper and lower operation knobs by a user, the guide pin provided at one end of the selected connecting shaft moves in a state of being pulled along the curved slit of the compound guide slits of the second module main body and simultaneously the operating bar of a corresponding connecting shaft is rotationally displaced by approximately 90 degrees while moving unidirectionally in a state of being pulled in a corresponding rectilinear through-bore. Thus, the slot-shaped hooking hole of the coupled member disposed at the end of the rotationally displaced operating bar is arranged in a crossing shape with a phase difference of approximately 90 degrees to the hooking piece of a corresponding coupling member that advances to the inside of the inner hollow part and is in a standby state.

Subsequently, when the selective rotation of any one of the upper and lower operation knobs is performed by a user, the guide pin moves linearly by a predetermined distance along the compound guide slit of the rectilinear section to cause the operating bar of a corresponding connecting shaft to move linearly. Thus, the front end of the insertion unit is bendingly operated in a vertical or horizontal direction depending on a pattern of the selective rotational operation of the operation knobs so that endoscopic surgery can be performed smoothly.

A hooking connection operation in which the slot-shaped hooking holes of the coupled members and the hooking pieces of the coupling members are hookingly connected to each other while the connecting shafts move in a state of being pulled by the selective rotational operation of the operation unit, a hooking connection operation, and a bending operation in which the operation wires extending from the rack gears in a hooking connection state are caused to move in a state of being pulled to bendingly operate the front end of the insertion unit can be performed sequentially.

Herein, although it has been illustrated and described that the selective rotational operation of the operation unit by a user is performed through any one of the upper and lower operation knobs so that the front end of the insertion unit is bendingly operated unidirectionally, i.e., in a vertical or horizontal direction, the present invention is not limited thereto, and the front end of the insertion unit may be bendingly operated simultaneously bidirectionally, i.e., in both vertical and horizontal directions through a simultaneous rotational operation of the upper and lower operation knobs by the user.

In the meantime, in the process in which a corresponding connecting shaft is pulled to one side by an external force caused by the selective rotational operation of the operation unit by the user, the elastic member disposed on the corresponding connecting shaft is compressingly deformed to generate an elastic restoring force.

Thus, when the selective rotational operation of the operation unit is stopped to release the external force applied to the operation unit, any one of the first, second, third and fourth connecting shafts moved in a state of being pulled by the elastic restoring force of the elastic member is moved toward the insertion unit.

In this case, the guide pin formed on the coupling member disposed at one end of the corresponding connecting shaft moves in a state of being pulled in the reverse direction along the curved slit, and the operating bar of the corresponding connecting shaft is rotationally displaced by approximately 90 degrees in a reverse direction to return to its initial position in a corresponding rectilinear through-bore. For this reason, the slot-shaped hooking hole of the coupled member disposed at one end of the rotationally displaced and returned operating bar returns to the same vertical state as that of the hooking piece of a corresponding coupling member which is in a standby state in a vertical arrangement ion the inner hollow part, so that the operating state of the slot-shaped hooking hole and the hooking piece is converted into a hooking connection release state corresponding to a hooking connection standby state without having to additionally provide a separate hooking connection release means such as a button member.

In this case, the insertion unit and the operation unit can be completely separated/decoupled from each other through a simple separation/decoupling operation of the ring-shaped coupling element that couples the rear end of the insertion unit and the front end of the operation unit to each other.

While the present invention has been described in connection with the exemplary embodiments illustrated in the drawings, they are merely illustrative and the invention is not limited to these embodiments and the accompanying drawings. It will be appreciated by a person having an ordinary skill in the art that various equivalent substitutions, modifications and variations of the embodiments can be made without departing from the spirit and scope of the present invention. Therefore, the true technical scope of the present invention should be defined by the technical spirit of the appended claims.

What is claimed is:
1. A detachable endoscope comprising:
an insertion unit including an illuminating and image pickup unit;
an operation unit configured to control movements of a front end of the insertion unit; and
a detachable unit disposed between the insertion unit and the operation unit and configured to detachably connect the insertion unit to the operation unit,
wherein the detachable unit comprises:
a first detachable module disposed in the insertion unit to be connected to first ends of operating wires arranged in the insertion unit; and
a second detachable module disposed in the operation unit to be connected to both ends of upper and lower chains wound around upper and lower sprockets of the operation unit,
wherein the second detachable module comprises:
a second module main body disposed adjacent to an end of the operation unit and having through-bores formed in a longitudinal direction of the operation unit;
connecting shafts respectively within the through-bores to reciprocate therein such that first ends of the connecting shafts are connected to the both ends of the upper and lower chains by means of connecting wires; and
coupled members respectively disposed at second ends of the connecting shafts so as to be selectively connected to coupling members disposed at the first detachable module,
wherein the coupling members are configured to be inserted into inner hollow parts formed in the coupled members such that, when at least one of the connecting shafts is rotated unidirectionally the respective coupled member and its corresponding coupling member are connected to each other by a hooking connection.

2. The detachable endoscope according to claim 1, wherein the connecting shafts respectively comprises:
one or more operating bars configured to be inserted into the through-bores to reciprocate therein and respectively including one or more elastic members; and
one or more guide pins disposed at first ends of the operating bars so as to rotationally displace the operating bars by moving in a curved pattern along guide slits formed to be incised on the second module main body,
wherein the coupled members are respectively disposed at first ends of the operating bars having the guide pins so as to be selectively connected to the coupling members.

3. The detachable endoscope according to claim 2, wherein the second module main body comprises:
a main body block having the through-bores formed therein and the guide slits formed to be incised on an outer surface thereof;
a first covering plate disposed at one end of the main body block and having a plurality of first through-holes penetratingly formed therein to allow first ends of the connecting shafts to advance to and retract from the plurality of first through-holes; and
a second covering plate disposed at another end of the main body block positioned corresponding to the first detachable module, and having a plurality of second through-holes penetratingly formed therein to correspond to the through-bores.

4. The detachable endoscope according to claim 3, wherein the one or more elastic members supports at first ends thereof against an inner surface of the first covering plate.

5. The detachable endoscope according to claim 3, wherein the guide slits comprise curved sections extending in a curved pattern from both sides of the main body block to top and bottom surfaces thereof, and linear sections extending by a predetermined length on the top and bottom surfaces of the main body block.

6. The detachable endoscope according to claim 1, wherein the coupled members comprise slot-shaped hooking holes formed therein to expose the inner hollow parts toward the coupling members, and the coupling members comprise plate-shaped hooking pieces formed at distal ends thereof so as to be widened at front ends thereof to both sides.

* * * * *